United States Patent
Evans et al.

(10) Patent No.: US 7,160,263 B2
(45) Date of Patent: Jan. 9, 2007

(54) PREFORMED ANKLE BRACE

(75) Inventors: John C. Evans, Nr Rochdale (GB); Martin O'Hara, Charlotte, NC (US)

(73) Assignee: BSN Medical, Inc., Wilmington, DE (US)

( * ) Notice: Subject to any disclaimer, the term of this patent is extended or adjusted under 35 U.S.C. 154(b) by 0 days.

(21) Appl. No.: 10/531,498

(22) PCT Filed: Apr. 15, 2003

(86) PCT No.: PCT/US03/11709

§ 371 (c)(1),
(2), (4) Date: Apr. 15, 2005

(87) PCT Pub. No.: WO2004/098467

PCT Pub. Date: Nov. 18, 2004

(65) Prior Publication Data

US 2006/0052734 A1 Mar. 9, 2006

(51) Int. Cl.
*A61F 5/00* (2006.01)

(52) U.S. Cl. .......................................... 602/23; 602/27

(58) Field of Classification Search .................... 602/5, 602/23, 27–29, 60–62, 65; 128/882, 892, 128/893

See application file for complete search history.

(56) References Cited

U.S. PATENT DOCUMENTS

| 4,966,134 | A | * | 10/1990 | Brewer ........................ 602/27 |
| 5,125,400 | A | | 6/1992 | Johnson, Jr. |
| 5,389,065 | A | * | 2/1995 | Johnson, Jr. ................. 602/27 |
| 5,445,602 | A | | 8/1995 | Grim et al. |
| 5,501,659 | A | * | 3/1996 | Morris et al. ................. 602/27 |
| 5,657,767 | A | * | 8/1997 | Nelson et al. ............... 128/882 |
| 5,944,678 | A | * | 8/1999 | Hubbard ..................... 602/27 |
| 6,406,450 | B1 | | 6/2002 | Kowalczyk et al. |

* cited by examiner

*Primary Examiner*—Michael A. Brown
(74) *Attorney, Agent, or Firm*—Adams Evans P.A.

(57) ABSTRACT

An ankle brace of the type adapted to extend along the lateral and medial aspects of an injured ankle and lower leg for supporting the ankle during healing. A medial and lateral side support are provided for extending along the respective medial lateral aspects of the ankle and lower leg and includes an elongate, rigid support members, each having a lower end of sufficiently narrow width and thinness to fit inside a shoe being worn by a wearer of the brace, A soft, flexible perimeter edge portion is mechanically adhered to and extends outwardly in overlapping, non-interfitting relation to the support members for protecting the leg and ankle from irritation resulting from contact with edges of the support members. A connector connects the medial side support and lateral side support together at their respective lower ends and extend under the foot of the wearer of the brace.

22 Claims, 12 Drawing Sheets

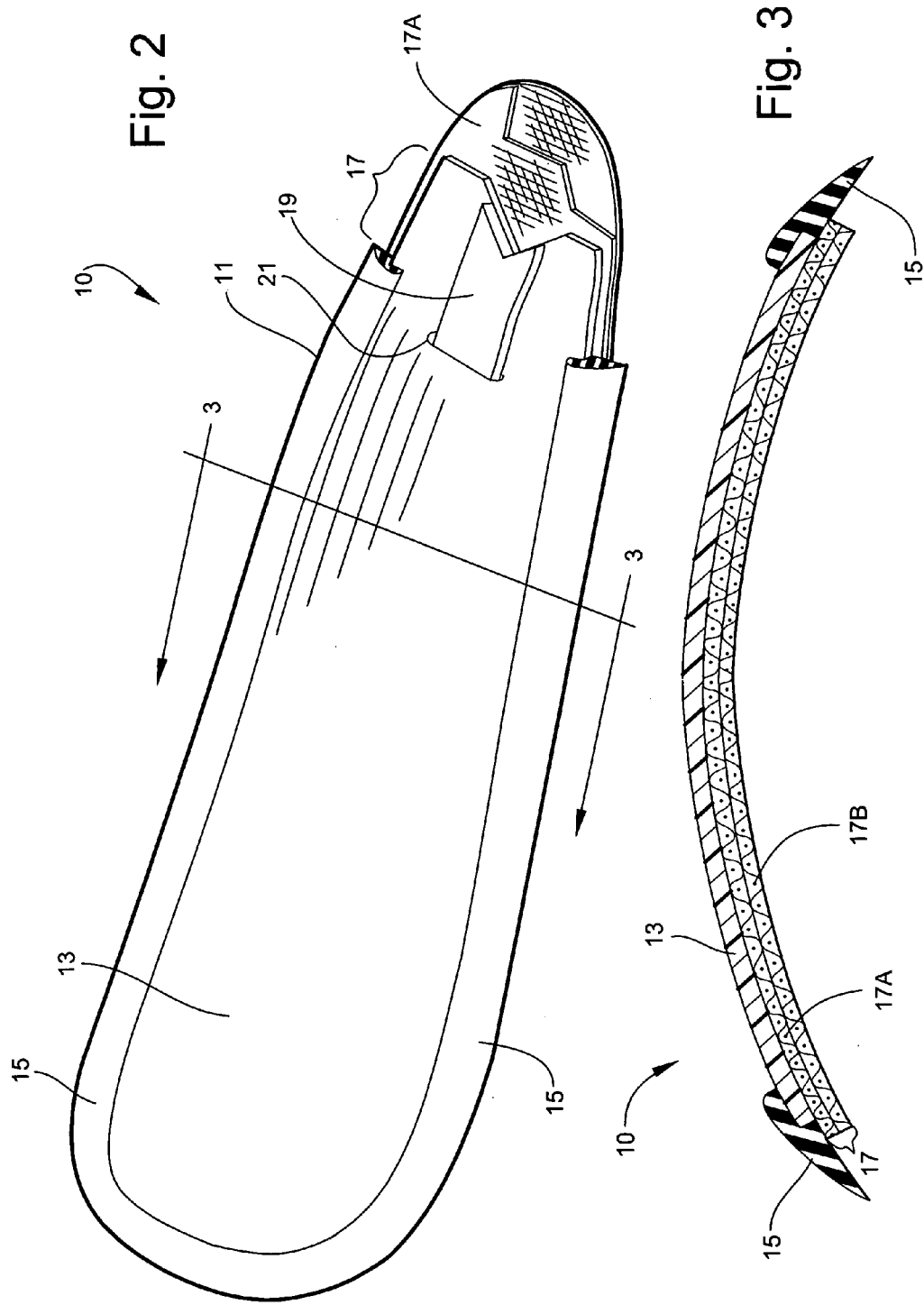

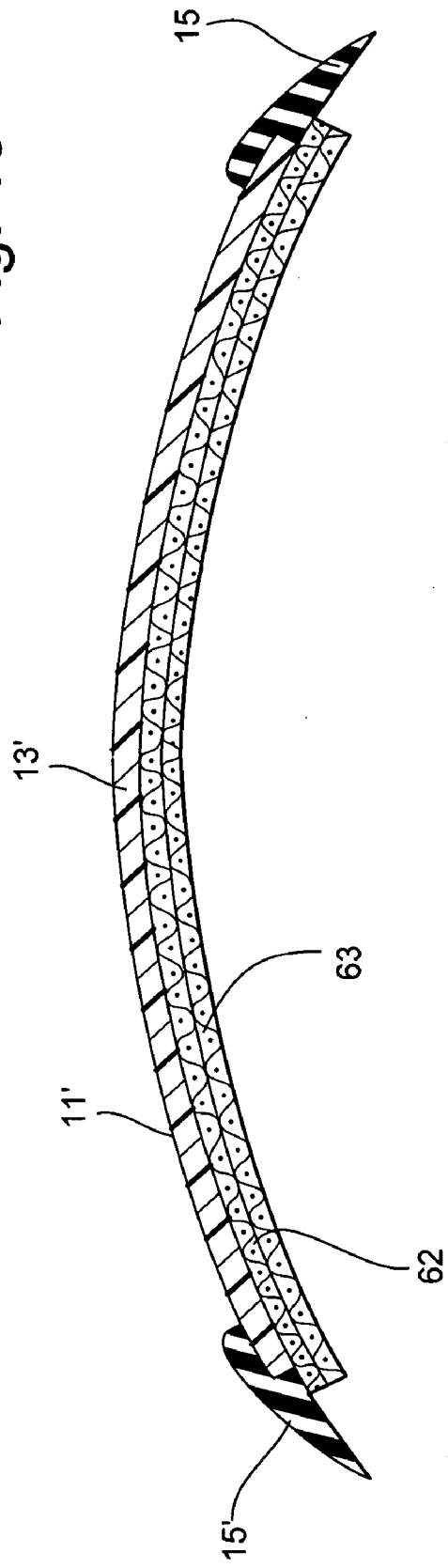

PREFORMED ANKLE BRACE

TECHNICAL FIELD AND BACKGROUND OF THE INVENTION

This invention relates to a preformed ankle brace that includes soft edge portions. The ankle brace also includes novel inner layers that provide comfort, cleanliness and washability in a lightweight, preformed brace product. The brace provides support to the lateral and medial aspects of the ankle and lower leg and stabilizes the ankle against inversion and eversion, while permitting normal dorsiflexion and plantarflexion of the ankle during healing. The brace is specifically designed to be worn with a shoe and is thus dimensionally configured to fit within a shoe.

The brace provides enhanced comfort by conforming to the medial and lateral aspects of the ankle and lower leg while providing edge portions that prevent contact between the skin and the hard shell portions of the brace.

The brace is simple, robust, and can be manufactured with relatively few manufacturing steps.

SUMMARY OF THE INVENTION

Therefore, it is an object of the invention to provide an ankle brace that includes soft edge portions.

It is another object of the invention to provide an ankle brace that includes inner padding that is comfortable and easy to clean.

It is another object of the invention to provide an ankle brace that includes both hard shell support elements and padding elements.

It is another object of the invention to provide an ankle brace that has an inner padding layer of variable thickness.

These and other objects of the present invention are achieved in the preferred embodiments disclosed below by providing an ankle brace of the type adapted to extend along the lateral and medial aspects of an injured ankle and lower leg for supporting the ankle during healing. A medial side support is provided for extending along the medial aspect of the ankle and lower leg. The medial side support includes an elongate, rigid support member having a lower end of sufficiently narrow width and thinness to fit inside a shoe being worn by a wearer of the brace. The medial side support includes a soft, flexible perimeter edge portion mechanically adhered to and extending outwardly in overlapping, non-interfitting relation to the medial support member for protecting the medial aspect of the leg and ankle from irritation resulting from contact with edges of the support member. A lateral side support extends along the lateral aspect of the ankle and lower leg, the lateral side support includes an elongate, rigid support member having a lower end of sufficiently narrow width and thinness to fit inside the shoe. The lateral support member includes a soft, flexible perimeter edge portion mechanically adhered to and extends outwardly in overlapping, non-interfitting relation to the support member for protecting the lateral aspect of the leg and ankle from irritation resulting from contact with edges of the rigid support member. Connector means connect the medial side support and lateral side support together at their respective lower ends and extend under the foot of the wearer of the brace.

According to one preferred embodiment of the invention, the medial side support and the lateral side support each include a padding material positioned adjacent an inner face of the respective rigid support members.

According to another preferred embodiment of the invention, the perimeter edge portions are adhered to the respective rigid support members by an adhesive.

According to yet another preferred embodiment of the invention, the padding material overlaps and extends outwardly beyond side edges of the respective side support members, and the perimeter edge portions overlap and extend outwardly beyond side edges of both the support members and the padding material.

According to yet another preferred embodiment of the invention, the medial rigid support members and the lateral rigid support member each are formed of a preformed plastic material.

According to yet another preferred embodiment of the invention, the padding material overlaps and extends outwardly beyond the side edges of the rigid support members. The perimeter edge portions overlap and extend outwardly beyond the side edges of both the rigid support members and the padding material, and the perimeter edge portions are adhered to both the rigid support members and to overlapped portions of the padding material.

Preferably, the padding material comprises a three-dimensional fabric.

According to yet another preferred embodiment of the invention, the padding material comprises two overlaid layers of a three-dimensional fabric.

According to yet another preferred embodiment of the invention, the padding material comprises at least one layer of a three-dimensional fabric of the type characterized by being highly air-permeable and free of latex.

According to yet another preferred embodiment of the invention, the brace includes at least one strap for retaining the medial side support and lateral side support in a closely-conforming condition against the lower leg and ankle.

According to yet another preferred embodiment of the invention, the padding material is between 6 and 12 mm thick.

According to yet another preferred embodiment of the invention, the padding material is 9 mm thick.

According to yet another preferred embodiment of the invention, the padding material comprises a single layer overlying the inner face of the rigid support member, and a second layer overlying an area of the rigid support member adapted to reside next to and support the ankle.

According to yet another preferred embodiment of the invention, the connector means comprises a medial strap carried by the medial support member, a lateral strap carried by the lateral support member, and complementary attachment members carried by the medial strap and lateral strap, respectively, for permitting the medial strap and the lateral strap to be releasably connected.

According to yet another preferred embodiment of the invention, the complementary attachment members comprise hook and loop fastener assemblies.

According to yet another preferred embodiment of the invention, the connector means comprises a strap carried by one of the medial support member or lateral support member having an attachment member carried on one end thereof, and a complementary attachment member carried on an outer surface of the other of the medial support member and the lateral support member for cooperating with the attachment member for connecting the medial side support and the lateral side support.

According to yet another preferred embodiment of the invention, the perimeter edge portion is selected from the group consisting of vinyl, rubber or synthetic rubber.

According to yet another preferred embodiment of the invention, the perimeter edge portion is tapered towards the outer edge thereof to increase flexibility.

According to yet another preferred embodiment of the invention, an ankle brace is provided of the type adapted to extend along the lateral and medial aspects of an injured ankle and lower leg for supporting the ankle during healing. The brace comprises a medial side support for extending along the medial aspect of the ankle and lower leg. The medial side support includes an elongate, rigid support member having a lower end of sufficiently narrow width and thinness to fit inside a shoe being worn by a wearer of the brace. The medial side support includes a soft, flexible perimeter edge portion mechanically adhered to and extending outwardly in overlapping, non-interfitting relation to the medial rigid support member for protecting the medial aspect of the leg and ankle from irritation resulting from contact with edges of the rigid support member. A lateral side support is provided for extending along the lateral aspect of the ankle and lower leg, the lateral side support including an elongate, rigid support member having a lower end of sufficiently narrow width and thinness to fit inside the shoe. The lateral side support includes a soft, flexible perimeter edge portion mechanically adhered to and extending outwardly in overlapping, non-interfitting relation to the lateral rigid support members for protecting the lateral aspect of the leg and ankle from irritation resulting from contact with edges of the rigid support member. Connector means connect the medial side support and lateral side support together at their respective lower ends and extend under the foot of the wearer of the brace. The connector means comprise a medial strap carried by the medial support member, and a lateral strap carried by the lateral support member. Complementary attachment members are carried by the medial strap and lateral strap, respectively, for permitting the medial strap and the lateral strap to be connected. The complementary attachment members comprise respective hook and loop fastener assemblies. At least one layer of fabric padding is positioned on an inner surface of the medial and lateral rigid support members for providing protection to the leg and ankle.

According to yet another preferred embodiment of the invention, the fabric padding extends outwardly beyond the perimeter of the rigid support member, the perimeter edge portion inwardly overlaps the edges of the rigid support member, and the perimeter edge portion outwardly overlaps the fabric padding to define an outermost perimetrical extent of the medial and lateral side supports of the ankle brace.

BRIEF DESCRIPTION OF THE DRAWINGS

Some of the objects of the invention have been set forth above. Other objects and advantages of the invention will appear as the invention proceeds when taken in conjunction with the following drawings, in which:

FIG. 2 is a perspective view with parts broken away of a side support of the brace;

FIG. 3 is a cross-sectional view taken through line 3—3 of FIG. 2;

FIG. 13 is a cross-sectional view taken through line 13—13 of FIG. 12.

DESCRIPTION OF THE PREFERRED EMBODIMENT AND BEST MODE

Figure 1:
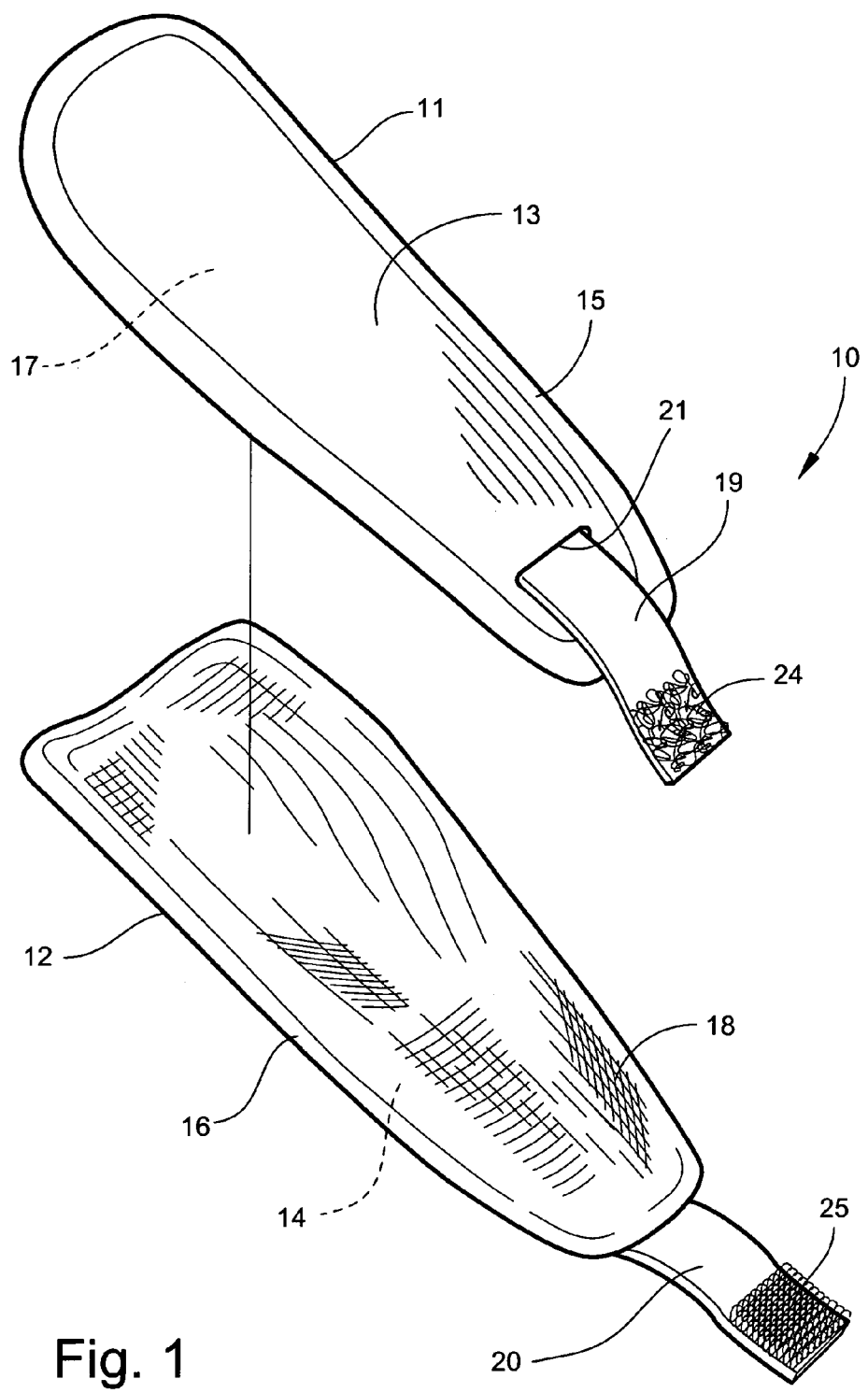
FIG. 1 is a perspective view of an ankle brace according to one embodiment of the invention.
Figure 4:
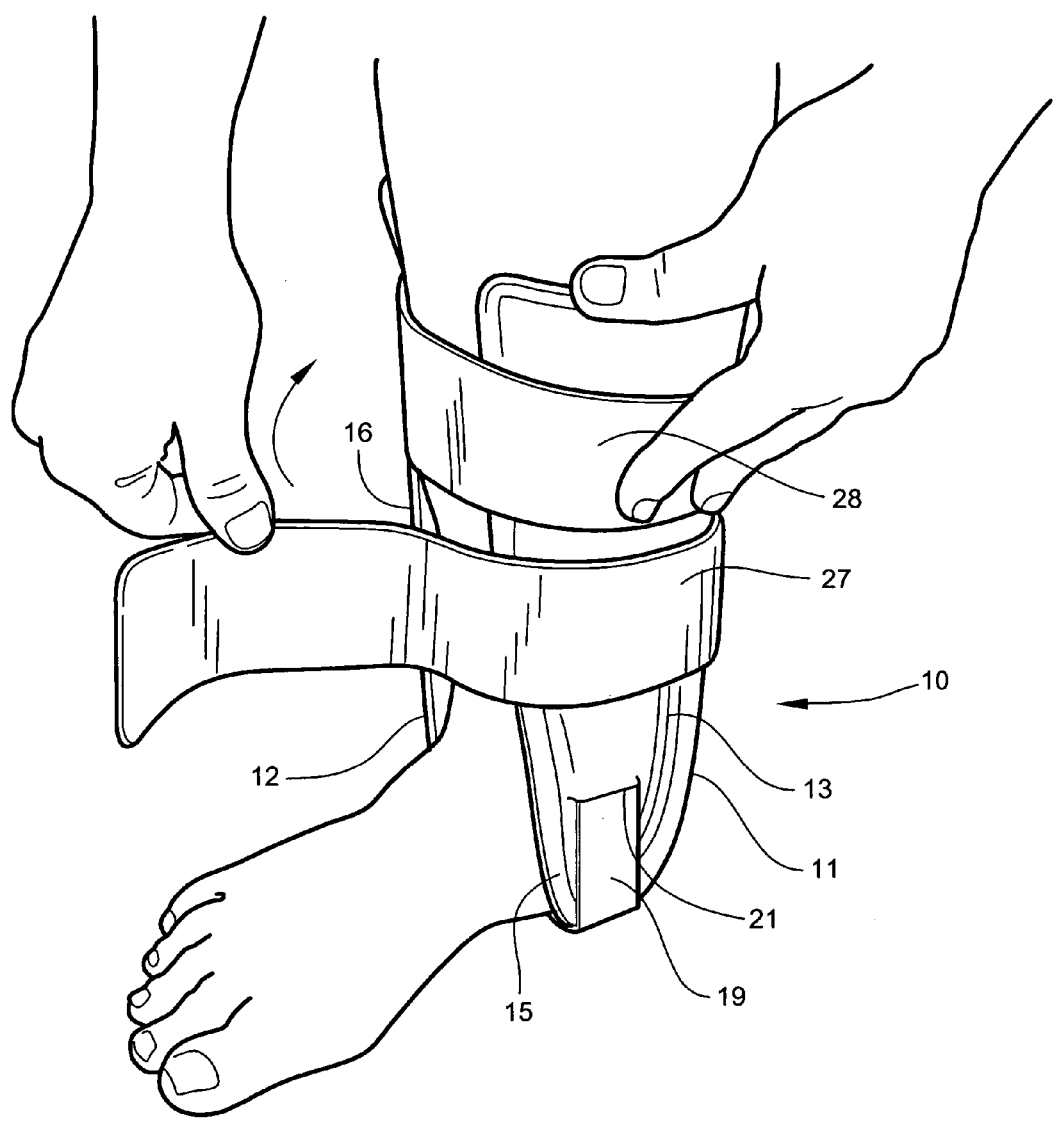
FIGS. 4–7 are perspective, medial, front and lateral views of the brace according to FIGS. 1–3 in place on a foot.
Figure 5:
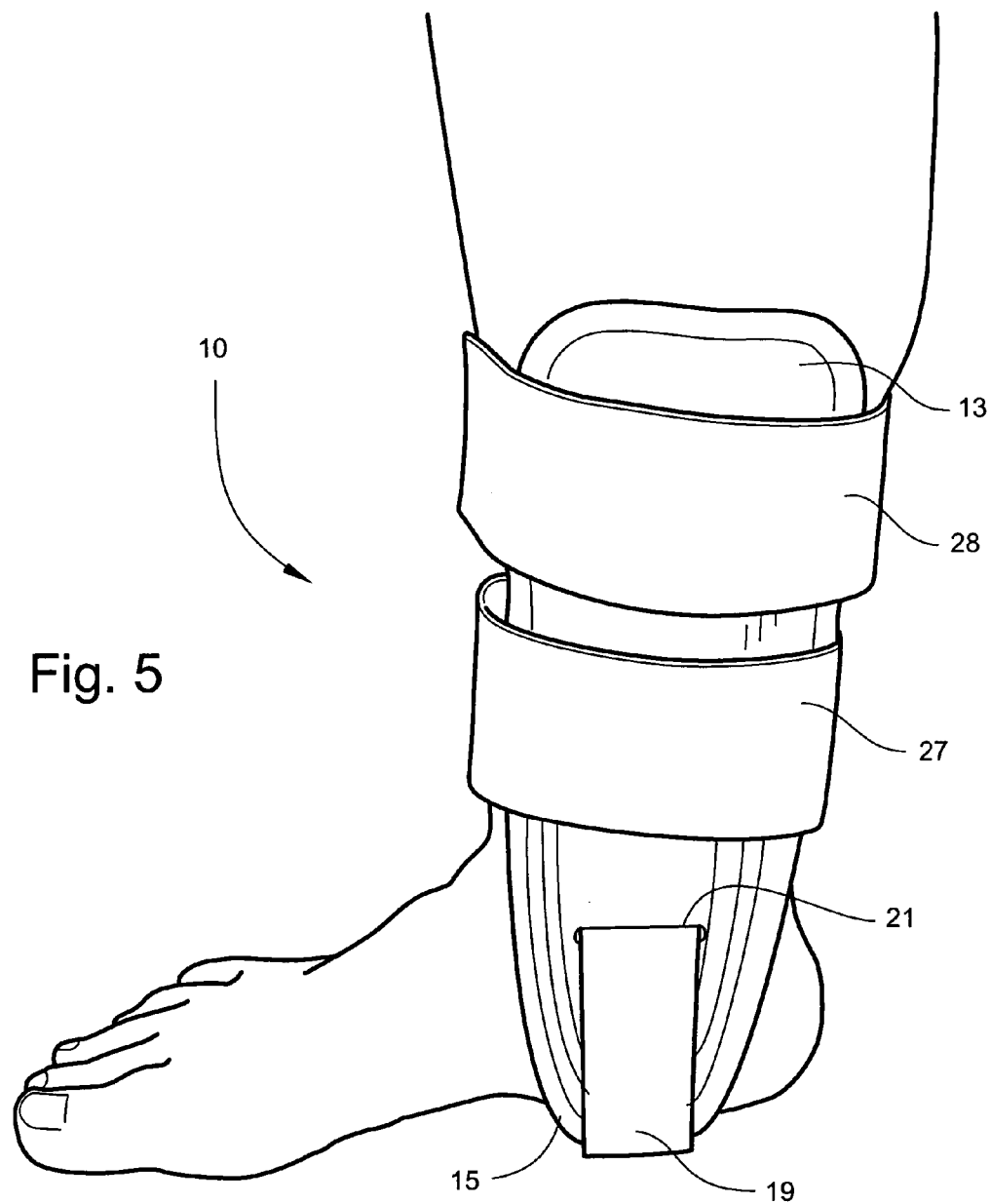
Figure 6:
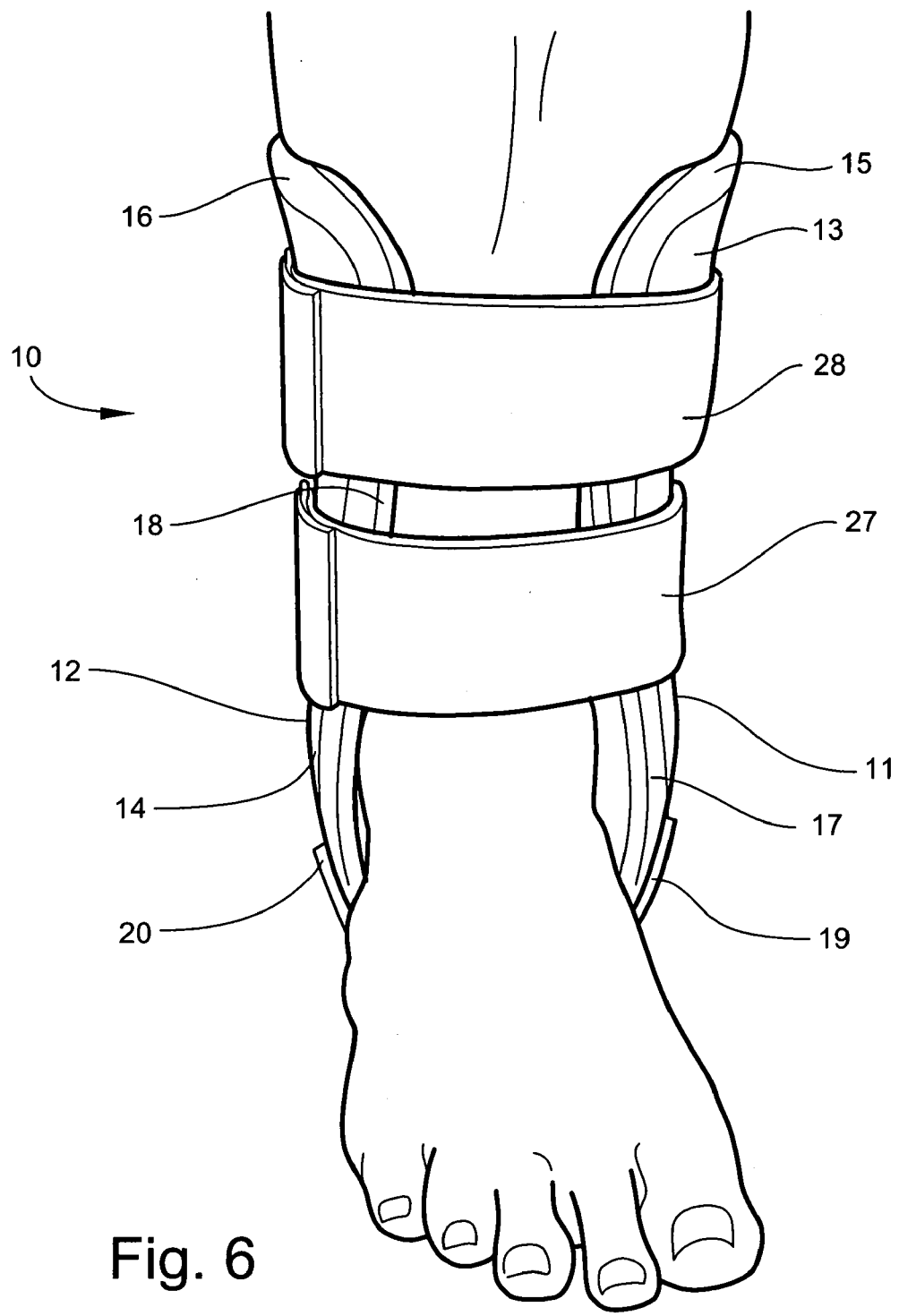

Referring now specifically to the drawings, a ankle brace according to the present invention is illustrated in FIG. 1 and shown generally at reference numeral 10. Ankle brace 10 is formed of a pair of side supports 11 and 12. The side supports 11 and 12 are preferably identical so that either can be used on the medial and lateral aspects of the lower leg and ankle.

The side supports 11 and 12 are formed of elongate rigid support members 13 and 14, respectively, each having a lower end of sufficiently narrow width and thinness to fit inside a shoe being worn by a wearer of the brace. The support members 13, 14 are preferably molded of thermoplastic material and are formed in a generally curved shape along the longitudinal axis so as to present an elongate concave surface to the lower leg and ankle being supported. Suitable materials include 12 melt polypropylene that is approximately 1.3 mm thick. The outside surface is preferably polished.

The side supports 11 and 12 also include respective soft, flexible perimeter edge portions 15, 16 mechanically adhered to and extending outwardly in overlapping, non-interfitting relation to the support members 13, 14 for protecting the medial aspect of the leg and ankle from irritation resulting from contact with edges of the rigid support member 13, 14. Suitable materials include vinyl, rubber, or thermoplastic elastomer such as that sold by Advanced Elastomer Systems under the trademark Santoprene®.

The inner, concave surface of the side supports 11 and 12 is covered with a padding material 17, 18, respectively, for protecting the lower leg and ankle from contact with the major concave surface of the rigid support members 13, 14. As is shown in FIG. 1, the padding material 17, not shown, and also 18, covers the full perimetrical extent of the side support members 13, 14 and thus provides full protection against contact except at the edges. The padding 17, 18 preferably does not extend outwardly to the outer perimeter of the flexible edge portions 15, 16, also shown in FIG. 1. Rather, the edge portions 15, 16 are left exposed and will typically be spaced from contact with the lower leg and ankle by at least some of the thickness of the padding material 17, 18. As movement occurs and the padding material 17, 18 is compressed, contact with the rigid support members 13, 14 is prevented by the flexible edge portions 15, 16, respectively.

A preferred padding material is a three-dimensional spacer fabric, such as a knitted spacer fabric manufactured by Tytex Group. Such fabrics are extremely light weight but nevertheless provide a robust cushioning effect for any given thickness and density. They serve well as substitutes for foam, elastic and neoprene, and are latex-free. Moisture transfer and high air permeability provide additional benefits in this particular application. Typical thicknesses of the padding material 17, 18 are in the range of 6–12 mm, with one preferred thickness being two layers of 4.5 mm, for a total of 9 mm. These thicknesses may be obtained by use of a single layer or multiple layers that collectively produce the desired thickness. The padding material 17, 18 is easily cut to shape by die-cutting, sonic cutting and welding or other suitable means, and is easily adhered to the concave inner face of the support members 11, 12 with any of a wide variety of known adhesives approved for use in medical applications. Alternatively, the padding material may be releasably adhered to the concave inner face of the side supports 11, 12 with attachment members such as hook-and-loop or other types of touch fasteners, not shown. Releasability provides the option of increasing or decreasing the thickness, density, air permeability or other characteristics of the padding, or replacing worn padding material 17, 18, while retaining the side supports 11 and 12.

The side supports 11 and 12 are connected and held in place in the shoe by a connector means, such as a pair of woven, knitted, nonwoven fabric or plastic straps 19, 20. As shown in FIG. 1, one manner of attaching the straps 19, 20 is to insert and attach one end of the strap 19 and 20 within a slot, shown by way of example at 21 on side support 11. The free end of the straps 19, 20 are provided with complementary patches of loops 24 and hooks 25. The patches of loops and hooks 24, 25 are sufficiently long that adjustment can be accomplished by the degree of overlap between the respective patches of loops and hooks 24, 25 while still providing a connection with adequate resistance to separation. As noted below, numerous other connection methods are possible.

Referring now to FIGS. 2 and 3, reference will be made to the side support 11 as exemplary of both side supports 11 and 12. The padding material 17 of side support 11 includes two layers 17A, 17B, of fabric padding material 17A, 17B underlying the rigid side support member 13 and an inner portion of the flexible edge portion 15. As best shown in FIG. 3, the side support 11 comprises an adhered lamination of the side support member 13 and the two layers of fabric padding material 17A, 17B. The flexible edge portion 15 is preferably mechanically adhered to both the side support member 13 and the underlying padding material layers 17A, 17B in an overlapping, non-interfering relation to the side support member 13. The flexible edge portion 15 is preferably adhered by a suitable adhesive.

Figure 7:
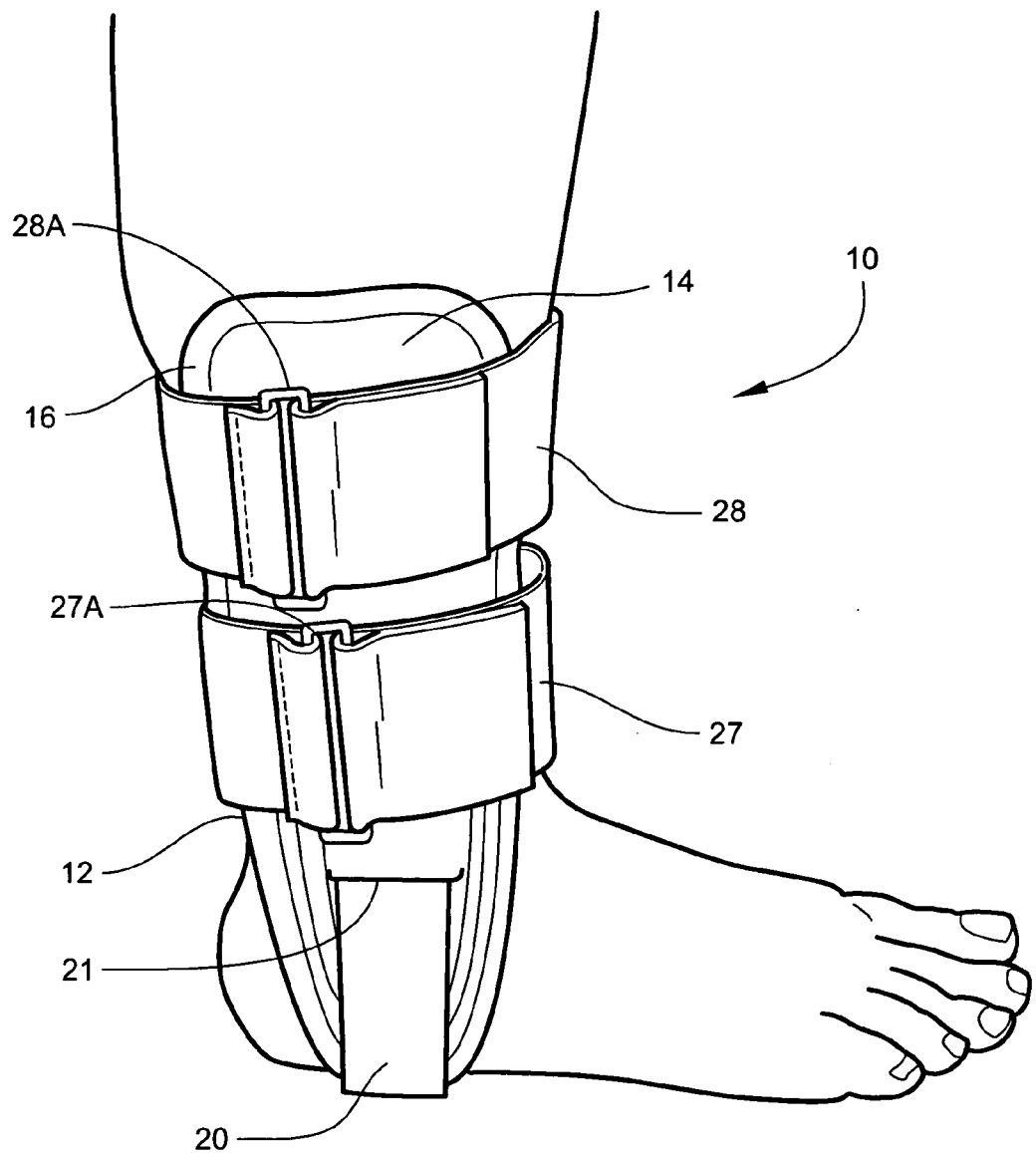

Referring now FIGS. 4–7, application of the brace 10 is straightforward, and includes attaching the straps 19 and 20, placing the attached straps 19, 20 under the heel, folding the side supports 11 and 12 up against the medial and lateral aspects, respectively, of the lower leg and ankle. The straps 19 and 20 are adjusted as needed. The brace 10 is then secured to the lower leg and ankle with, for example, straps 27, 28. Straps 27, 28 may be either elastic or inelastic, and typically may include complementary hook and loop material to secure the straps 27, 28 in the desired position. As best shown in FIG. 7, the straps 27, 28 may include buckles 27A, 28A, respectively to assist in adjusting and securing the straps in place. Alternatively, an elastic wrap, not shown, may be used. The brace 10 may be worn either over or under a sock.

Figure 8:
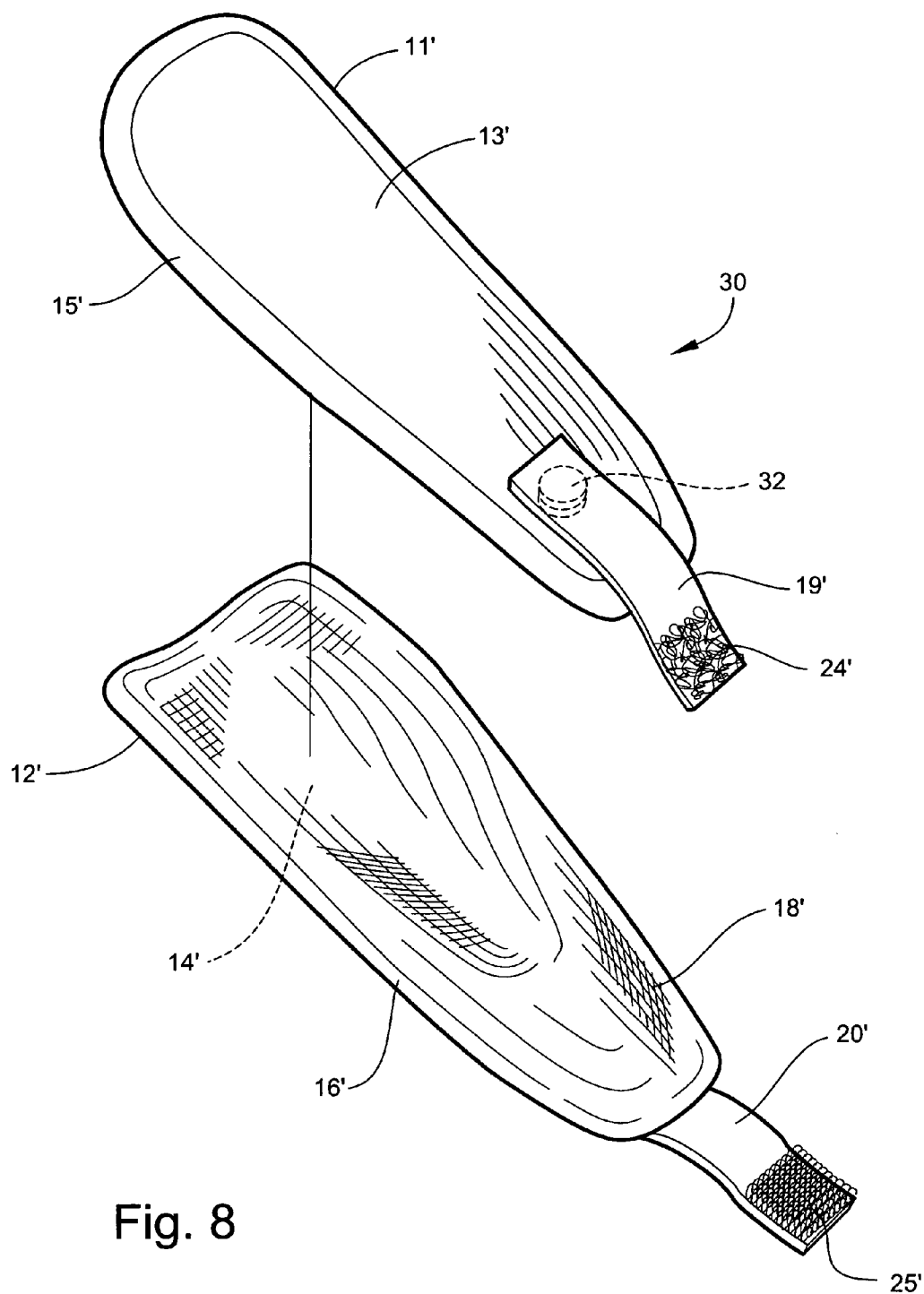
FIG. 8 is a perspective view of an ankle brace according to another embodiment of the invention.

Referring now to FIG. 8, a brace 30 is shown, prime notation indicating elements in common with FIGS. 1–7. The straps 19' and 20' are secured to the rigid support members 13 and 14 by a pivotable rivet 32, one shown on the support member 13. The rivet 32 requires only a small hole instead of a slot, and allows the straps 19', 20' to rotate if necessary to accommodate the size and shape of the foot in relation to the lower leg.

Figure 9:
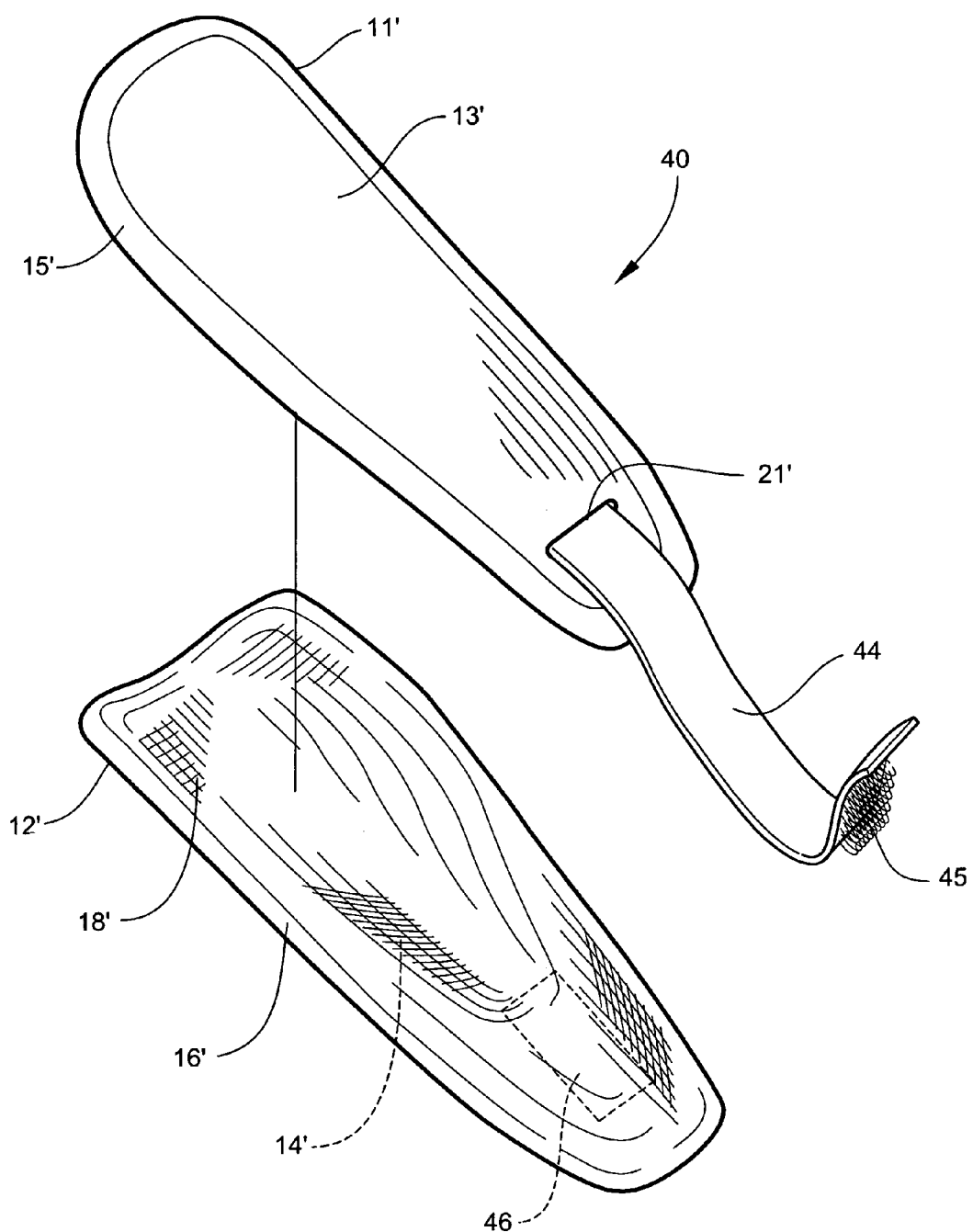
FIG. 9 is a perspective view of an ankle brace according to yet another embodiment of the invention.
Figure 10:
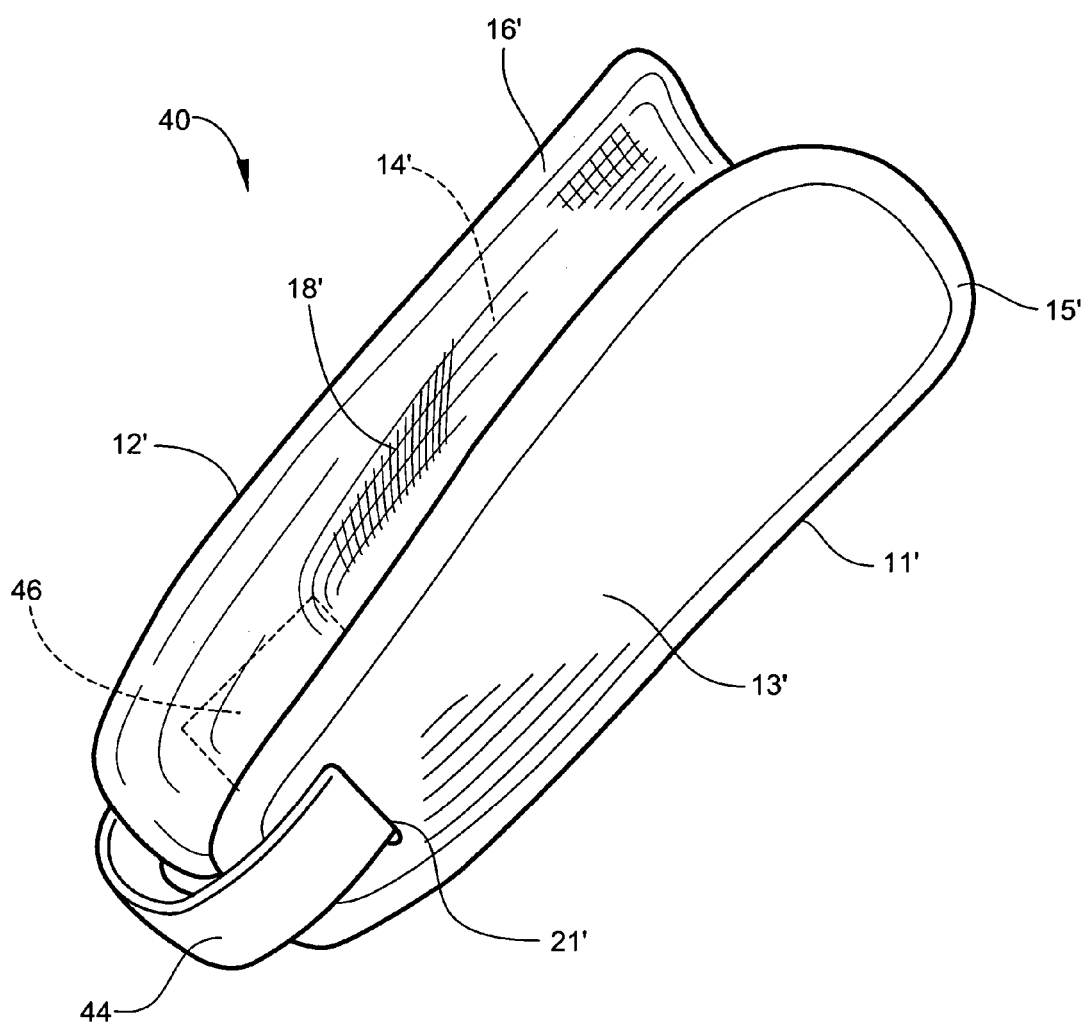
FIG. 10 is a perspective view of the ankle brace according to FIG. 9 in position to be placed on the ankle leg of the wearer.

Referring now to FIGS. 9 and 10, a brace 40 is shown, prime notation indicating elements in common with FIGS. 1–7. A strap 44 is secured to the rigid support members 13' and 14' by insertion into a slot 21', and attachment to the rigid support member 13' within the slot 21'. The strap 44 is sufficiently long to extend under the foot and up opposing side of the ankle to attach with a mating patch of complementary attachment material. For example, by placement of a patch of hook material 45 on one face of the strap 44, the strap 44 mates with a complementary patch of loop material 46 on the outer face of the support member 14'. The length of the patch of hook material 45 and the loop material 45 is sufficiently long to permit adjustment to the extent necessary to accommodate a predetermined size range. Of course, the rivet 32 shown in FIG. 8 could be used on the embodiment shown in FIGS. 8 and 9, as well.

Figure 11:
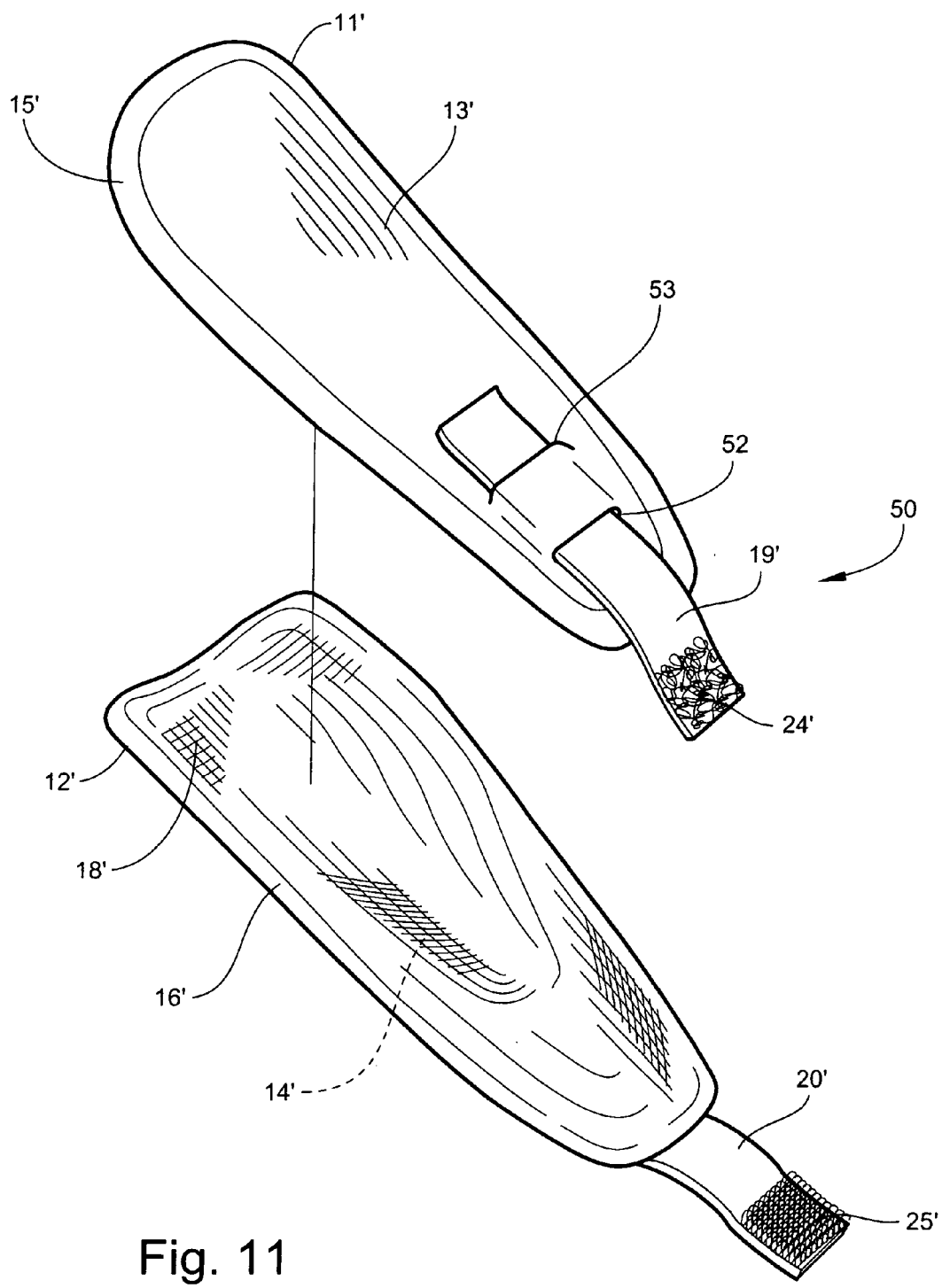
FIG. 11 is a perspective view of an ankle brace according to yet another embodiment of the invention.

Referring now to FIG. 11, a brace 50 is shown, prime notation indicating elements in common with FIGS. 1–7. The straps 19' and 20' are secured to the rigid support members 13' and 14' by a means of a pair of spaced-apart slots 52, 53, shown on the support member 13'. The straps 19', 20' and the slots 52, 53 are sized so that the straps 19', 20' are frictionally-retained at a given position, thus permitting adjustment by the wearer by pulling or pushing the straps 19', 20' as required for proper adjustment and comfort without removing the brace 50.

Figure 12:
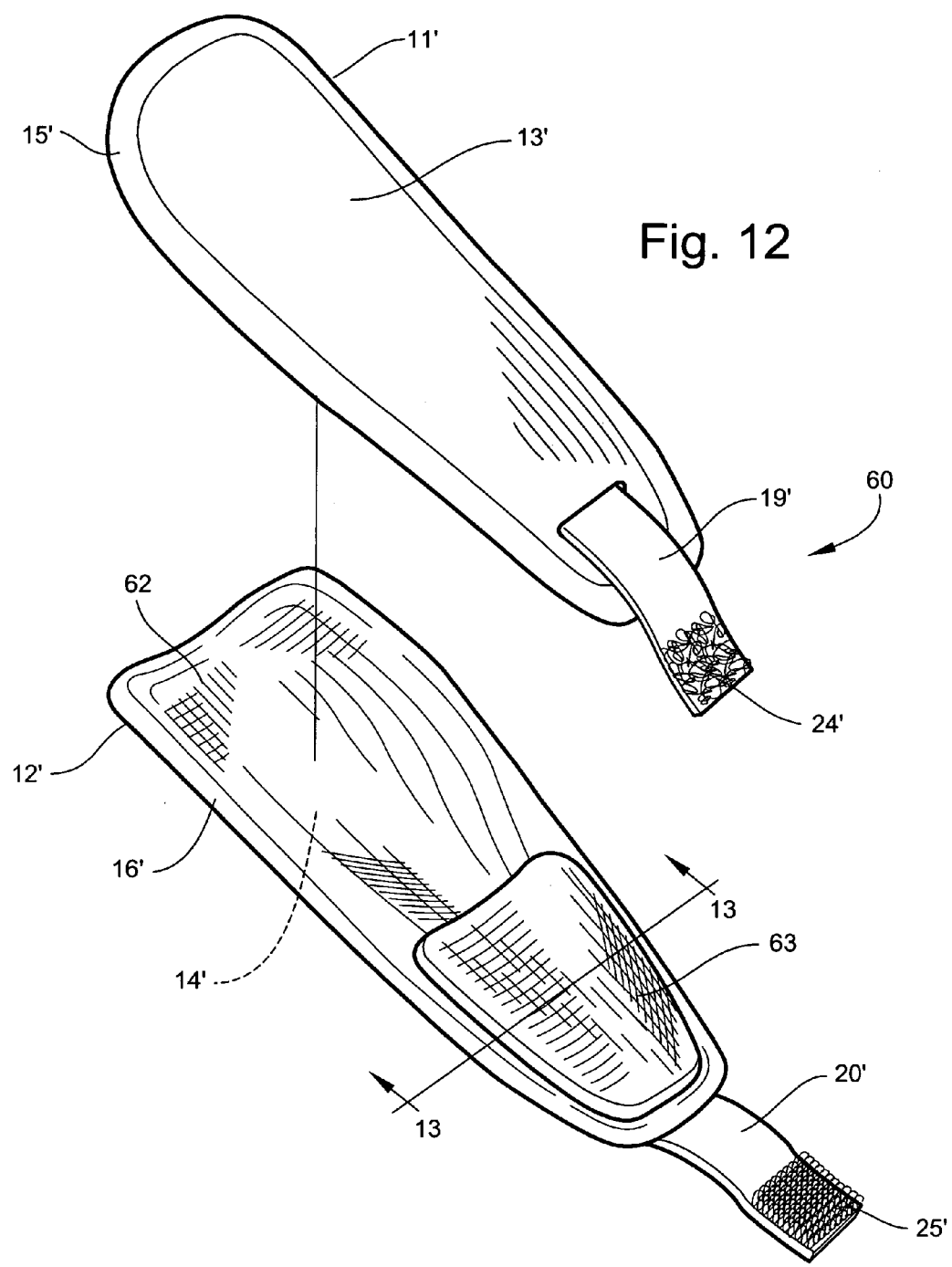
FIG. 12 is a perspective view of an ankle brace according to yet another embodiment of the invention.

Referring now to FIGS. 12 and 13, a brace 60 according to a further embodiment of the invention is shown, prime notation indicating elements in common with FIGS. 1–7. The padding material is provided in a single layer 62 that covers the full perimetrical extent of the side support members 13', 14' and thus provides full protection against contact except at the edges. A second layer of padding material 63 is shaped and sized to fit onto the area of the ankle defined by the medial malleolus and lateral malleolus, thus providing additional protection for these prominences.

A ankle brace is described above. Various details of the invention may be changed without departing from its scope. Furthermore, the foregoing description of the preferred embodiment of the invention and the best mode for practicing the invention are provided for the purpose of illustration only and not for the purpose of limitation—the invention being defined by the claims.

We claim:

1. An ankle brace of the type adapted to extend along the lateral and medial aspects of an injured ankle and lower leg for supporting the ankle during healing, and comprising:
   (a) a medial side support for extending along the medial aspect of the ankle and lower leg, the medial side support including an elongate, rigid support member having a lower end of sufficiently narrow width and thinness to fit inside a shoe being worn by a wearer of the brace, said medial side support including a soft, flexible perimeter edge portion mechanically adhered to and extending outwardly in overlapping, non-interfitting relation to the rigid support member for protecting the medial aspect of the leg and ankle from irritation resulting from contact with edges of the rigid support member;
   (b) a lateral side support for extending along the lateral aspect of the ankle and lower leg, the lateral side support including an elongate, rigid support member having a lower end of sufficiently narrow width and thinness to fit inside the shoe, said lateral side support including a soft, flexible perimeter edge portion mechanically adhered to and extending outwardly in overlapping, non-interfitting relation to the rigid support member for protecting the lateral aspect of the leg and ankle from irritation resulting from contact with edges of the rigid support member; and
   (c) connector means for connecting the medial side support and lateral side support together at their respective lower ends and extending under the foot of the wearer of the brace.

2. An ankle brace according to claim 1, wherein the medial side support and the lateral side support each include a padding material positioned adjacent an inner face of the respective rigid support members.

3. An ankle brace according to claim 1, wherein the perimeter edge portions are adhered to the respective rigid support members by an adhesive.

4. An ankle brace according to claim 1, wherein the padding material overlaps and extends outwardly beyond side edges of the respective rigid support members, and the perimeter edge portions overlap and extend outwardly beyond side edges of both the rigid support members and the padding material.

5. An ankle brace according to claim 1, 2, 3 or 4, wherein the medial support member and the lateral support member each are formed of a preformed plastic material.

6. An ankle brace according to claim 4, wherein:
(a) said padding material overlaps and extends outwardly beyond the side edges of the rigid support members;
(b) said perimeter edge portions overlap and extend outwardly beyond the side edges of both the rigid support member and the padding material; and
(c) said perimeter edge portions are adhered to both the rigid side support and to overlapped portions of the padding material.

7. An ankle brace according to claim 5, wherein said padding material comprises a three-dimensional fabric.

8. An ankle brace according to claim 5, wherein said padding material comprises two overlaid layers of a three-dimensional fabric.

9. An ankle brace according to claim 5, wherein said padding material comprises at least one layer of a three-dimensional fabric of the type characterized by being highly air-permeable and free of latex.

10. An ankle brace according to claim 1, and including at least one strap for retaining the medial side support and lateral side support in a closely-conforming condition against the lower leg and ankle.

11. An ankle brace according to claim 9, wherein said padding material is between 6 and 12 mm thick.

12. An ankle brace according to claim 9, wherein said padding material is 9 mm thick.

13. An ankle brace according to claim 2, wherein the padding material comprises:
(a) a single layer overlying the inner face of the rigid support members; and
(b) a second layer overlying an area of the rigid support member adapted to reside next to and support the ankle.

14. An ankle brace according to claim 13, wherein the padding material comprises a three-dimensional fabric.

15. An ankle brace according to claim 1, wherein said connector means comprises:
(a) a medial strap carried by the medial support member;
(b) a lateral strap carried by the lateral support member; and
(c) complementary attachment members carried by the medial strap and lateral strap, respectively, for permitting the medial strap and the lateral strap to be releasably connected.

16. An ankle brace according to claim 15, wherein said complementary attachment members comprise hook and loop fastener assemblies.

17. An ankle brace according to claim 1, wherein said connector means comprises:
(a) a strap carried by one of the medial support member or lateral support member having an attachment member carried on one end thereof;
(b) a complementary attachment member carried on an outer surface of the other of the medial support member and the lateral support member for cooperating with the attachment member for connecting the medial side support and the lateral side support.

18. An ankle brace according to claim 1, wherein said perimeter edge portion is selected from the group consisting of vinyl, rubber or synthetic rubber.

19. An ankle brace according to claim 1, wherein said perimeter edge portion is tapered towards the outer edge thereof to increase flexibility.

20. An ankle brace of the type adapted to extend along the lateral and medial aspects of an injured ankle and lower leg for supporting the ankle during healing, and comprising:
(a) a medial side support for extending along the medial aspect of the ankle and lower leg, the medial side support including an elongate, rigid support member having a lower end of sufficiently narrow width and thinness to fit inside a shoe being worn by a wearer of the brace, said medial side support including a soft, flexible perimeter edge portion mechanically adhered to and extending outwardly in overlapping, non-interfitting relation to the medial rigid support member for protecting the medial aspect of the leg and ankle from irritation resulting from contact with edges of the rigid support member;
(b) a lateral side support for extending along the lateral aspect of the ankle and lower leg, the lateral side support including an elongate, rigid support member having a lower end of sufficiently narrow width and thinness to fit inside the shoe, said lateral side support including a soft, flexible perimeter edge portion mechanically adhered to and extending outwardly in overlapping, non-interfitting relation to the lateral support member for protecting the lateral aspect of the leg and ankle from irritation resulting from contact with edges of the rigid support member;
(c) connector means for connecting the medial side support and lateral side support together at their respective lower ends and extending under the foot of the wearer of the brace, the connector means comprising:
(i) a medial strap carried by the medial support member;
(ii) a lateral strap carried by the lateral support member; and
(iii) complementary attachment members carried by the medial strap and lateral strap, respectively, for permitting the medial strap and the lateral strap to be connected, said complementary attachment members comprising respective hook and loop fastener assemblies; and
(d) at least one layer of fabric padding positioned on an inner surface of the medial and lateral rigid support members for providing protection to the leg and ankle.

21. An ankle brace according to claim 20, wherein the perimeter edge portions are adhered to an outer facing surface of the respective medial and lateral side supports.

22. An ankle brace according to claim 21, wherein:
(a) the fabric padding extends outwardly beyond the perimeter of the rigid support member;
(b) the perimeter edge portion inwardly overlaps the edges of the rigid support member; and
(c) the perimeter edge portion outwardly overlaps the fabric padding to define an outermost perimetrical extent of the medial and lateral side supports of the ankle brace.

* * * * *